United States Patent

Kawamura et al.

[11] Patent Number: 6,046,804
[45] Date of Patent: Apr. 4, 2000

[54] SAMPLE CELL FOR POLARIMETRY, POLARIMETER, AND POLARIMETRY

[75] Inventors: Tatsurou Kawamura, Kyotanabe; Jinsei Miyazaki, Higashiosaka; Akihito Kamei, Hirakata, all of Japan

[73] Assignee: Matsushita Electric Industrial Co., Ltd., Osaka, Japan

[21] Appl. No.: 09/149,084

[22] Filed: Sep. 8, 1998

[30] Foreign Application Priority Data

| Sep. 9, 1997 | [JP] | Japan | 9-243835 |
| Sep. 19, 1997 | [JP] | Japan | 9-254536 |
| May 25, 1998 | [JP] | Japan | 10-142733 |

[51] Int. Cl.$^7$ ................................................. G01N 21/01
[52] U.S. Cl. ........................... 356/244; 356/246; 250/343
[58] Field of Search ................................. 356/319, 364, 356/367, 368, 244, 246; 250/343

[56] References Cited

U.S. PATENT DOCUMENTS

| 3,312,141 | 4/1967 | Cary | 356/376 |
| 3,740,151 | 6/1973 | Chaney et al. | 356/117 |
| 3,817,629 | 6/1974 | Witte | 356/244 |
| 4,589,776 | 5/1986 | Carver et al. | 356/367 |
| 4,736,103 | 4/1988 | Nelson et al. | 250/343 |
| 4,902,134 | 2/1990 | Spanier | 356/364 |
| 4,988,199 | 1/1991 | Paul | 356/368 |
| 5,146,283 | 9/1992 | Parnoff et al. | 356/246 |
| 5,436,457 | 7/1995 | Tomita | 250/343 |
| 5,680,209 | 10/1997 | Machler | 356/319 |

FOREIGN PATENT DOCUMENTS

| 0 089 157 | 9/1983 | European Pat. Off. . |
| 20 40 481 | 2/1972 | Germany . |
| 22 29 723 | 1/1974 | Germany . |
| 2 197 467 | 5/1988 | United Kingdom . |

*Primary Examiner*—Frank G. Font
*Assistant Examiner*—Roy M. Punnoose
*Attorney, Agent, or Firm*—McDermott, Will & Emery

[57] ABSTRACT

A sample cell for polarimetry is disclosed. It comprises: a base member having a tubular cavity for holding a specimen and for permitting a light to transmit therethrough, and a pair of light-transmitting windows for sealing a pair of open ends of the cavity; and a coil arranged around the base member for generating a magnetic field inside the cavity along an axial direction of the cavity. The specimen is supplied to the cavity through a channel for communicating the cavity with the outside.

12 Claims, 9 Drawing Sheets

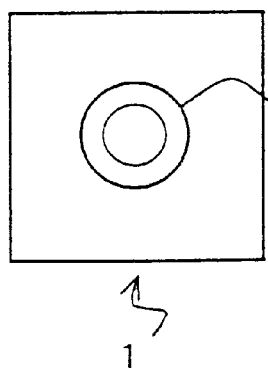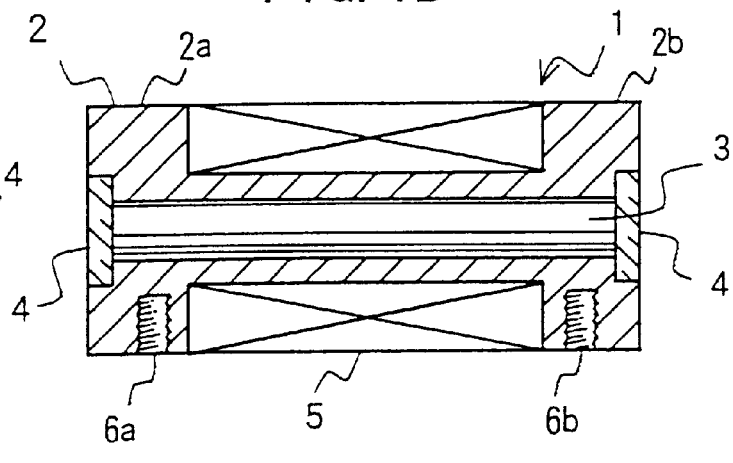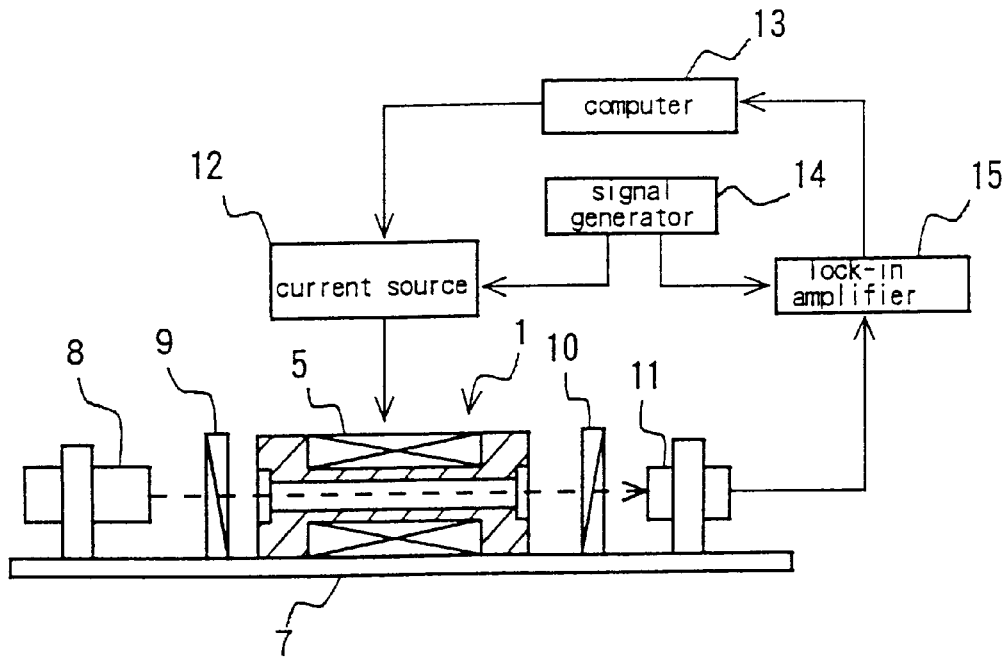

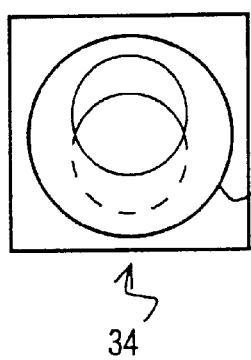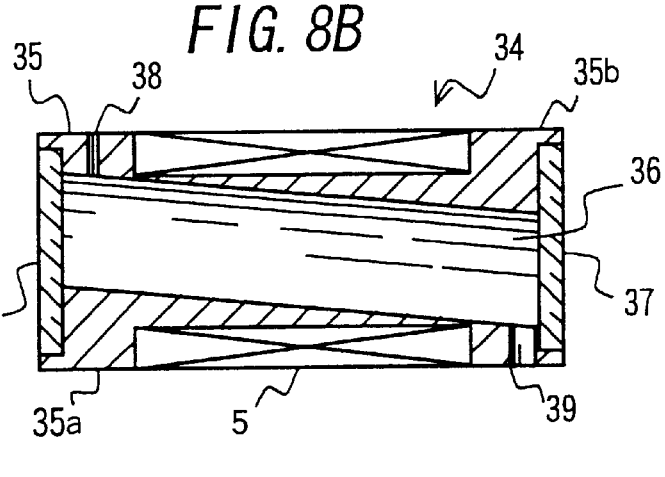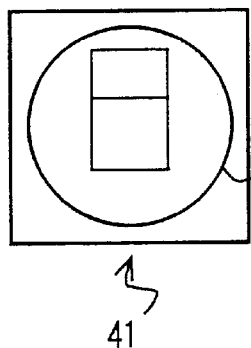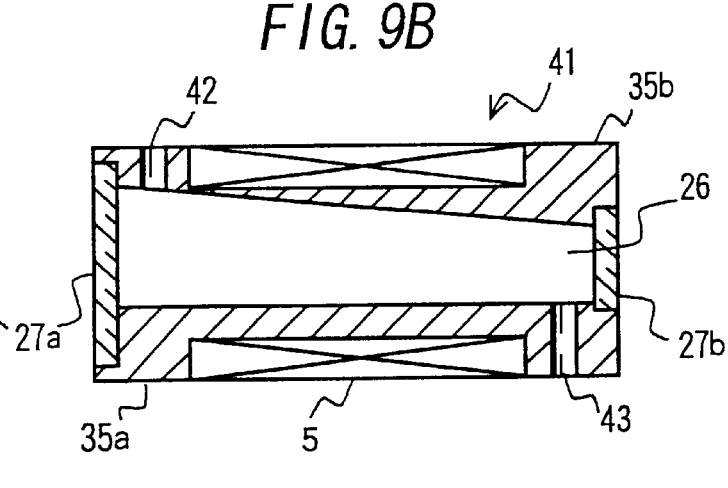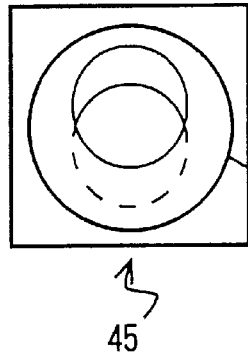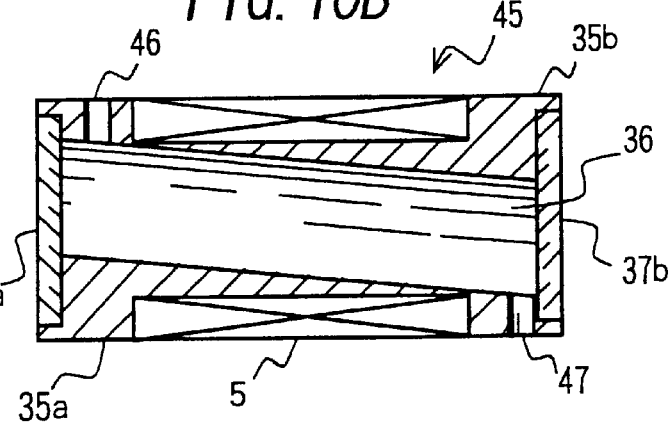

SAMPLE CELL FOR POLARIMETRY, POLARIMETER, AND POLARIMETRY

BACKGROUND OF THE INVENTION

The present invention generally relates to polarimetry (measurement on optical activity of specimen, expressed in angle of rotation), and more particularly to an improvement in a sample cell for accommodating a liquid specimen subjected to the polarimetry.

The polarimetry has heretofore been applied to identification, examination on purity, determination, and the like of a solute in a liquid specimen. Specifically, the polarimetry is employed in determining the concentrations of fructose, sucrose, glucose and the like contained in an aqueous solution. In recent years, an application of the polarimetry to an examination of urine sugar value (glucose concentration) or urine protein value (albumin concentration) is also proposed (International Patent Publication No. WO 97/18,470).

An angle of rotation "α" of a solution containing optically active substance is directly proportional to a product of a specific rotatory power "[α]" of the optically active substance and a concentration "C" thereof. If it is assumed that the length of the light path for the measurement is "L", then the angle "α" is represented by the following equation (1):

$$\alpha[\text{degree}] = L[\text{cm}] \times [\alpha] \times C[\text{kg/dl}] \tag{1}$$

It is therefore possible to derive a concentration of the optically active substance contained in the liquid specimen by measuring the angle of rotation of the liquid specimen.

One of the conventional methods of examining sugar or protein in a urine includes a use of a test paper impregnated with a reagent. The test paper is dipped in the urine and a color reaction thereof is observed by a spectrophotometer or the like. In this method, expendable supplies such as test papers are required.

Glucose and albumin in the urine demonstrate optical activities but the other components in the urine do not demonstrate the optical activity. In view of this point, the above publication proposes derivations of the urine sugar value and urine protein value by the polarimetry on the urine. According to this method, even if the glucose or the albumin contained in the urine is small, it is possible to determine the urine sugar value or urine protein value without using any expendable supplies. In this publication, the rotated angle of the plane of vibration i.e., the angle of rotation, is directly derived by projecting a light having a particular plane of vibration on a specimen to be detected and detecting a plane of vibration of the light transmitted through the specimen by using a rotary analyzer.

An example of the conventional polarimeter is shown in FIG. 15. A light source 81 configured with a sodium lamp, a band-pass filter, a lens, a slit and the like projects a substantially parallel light composed of a sodium D ray having a wavelength of 589 nm. A polarizer 82 transmits only a component that has a specific plane of vibration coincident with a transmission axis thereof, out of the light projected from the light source 81. A sample cell 83 for holding a specimen to be determined is arranged so that the light transmitted through the polarizer 82 can transmit therethrough. An analyzer 84 transmits only a component that has another specific plane of vibration, out of the light transmitted through the sample cell 83. An analyzer rotator 85 is for rotating the transmission axis of the analyzer 84 in a plane perpendicular to the direction of the advance of the light. An photosensor 86 is for detecting the light transmitted through the analyzer 84. The computer 87 controls the analyzer rotator 85 while recording and analyzing an output signal from the photosensor 86.

The principle of this polarimeter for the measurement will be explained as follows. In FIG. 16, the abscissa represents the relative angle "Θ" formed between the light transmission axis of the polarizer 82 and the light transmission axis of the analyzer 84, and the ordinate represents an intensity "I" of the light that has reached the photosensor 86, i.e., the output signal of the photosensor 86. Herein, the solid line indicates the output signal in the case where the specimen to be determined demonstrates no optical activity. Under this condition, the relationship between "Θ" and "I" is represented by the following equation (2):

$$I = T \times I_o \times (\cos \Theta)^2 \tag{2}$$

where, "T" is transmittance of the specimen, and "$I_o$" is an intensity of the light incident upon the specimen. Herein, a transmission loss and a reference loss of the sample cell 83 and the analyzer 84 respectively are ignored. As shown, a point where "I" reaches its minimum (hereinafter, to be referred to as "extinction point") appears for every π with the variation in "Θ", i.e., the rotation of the analyzer 84.

In a case wherein the specimen demonstrates an optical activity and its angle of rotation is "α", the intensity "$I_\alpha$" of the light that reaches the photosensor is represented by the dashed line in FIG. 16. The intensity "$I_\alpha$" is given by the following equation (3):

$$I_\alpha = T \times I_o \times \{\cos(\Theta - \alpha)\}^2 \tag{3}$$

As seen from this, the extinction point of the specimen which demonstrates an optical activity displaces by "α" as compared with that of the specimen which does not demonstrate the optical activity. It is therefore possible to measure the angle of rotation by finding the displacement of the extinction point by the computer 87. In the case of such polarimeter, S/N ratio in the output signal of the photosensor 86 is however comparatively inferior and it is difficult to accurately determine the position of the extinction point. As a result, it is difficult to measure the specimen having a small angle of rotation with high accuracy.

For this reason, there has been proposed another polarimeter which makes use of optical Faraday Effect, i.e., a phenomenon that when a light is permitted to transmit through a medium while being applied a magnetic field along the direction of its transmission, the direction of polarization of the light rotates with the advance of the light.

The optical Faraday Effect is represented by the following equation (4):

$$a = V \times H \times L \tag{4}$$

where, "a" represents an angle of rotation of the plane of vibration of the light [minute], "V" is Verdet's constant of the medium [minute/A] and "L" is a distance of transmission [m]. Herein, "V" varies with a medium, wavelength of light or temperature.

As one which utilizes this optical Faraday effect, there is an optical Faraday modulator. The optical Faraday modulator includes, for instance, a rod of flint glass and a solenoid coil configured around the rod. When a current is flown through the solenoid coil for generating a magnetic field inside the rod while permitting a light to transmit through the rod along an axis of the rod, the plane of vibration of the light propagating inside the rod rotates. By controlling the intensity of the current flown through the solenoid coil, it is possible to vary the angle of rotation of the plane of vibration at will.

An example of the polarimeter which employs the optical Faraday modulator is shown in FIG. 17. In this figure, parts and components which are identical with those used in the polarimeter shown in FIG. 15 are tagged with the same reference numerals.

The optical Faraday modulator 88 vibrates the plane of vibration of a light transmitted through a polarizer 82 by a modulation signal from a signal generator 89. A lock-in amplifier 90 is for phase sensitive detection of an output signal from the photosensor 86 with reference to the vibration-modulated signal from the optical Faraday modulator 88.

In FIG. 18, the abscissa and the ordinate represent "Θ" and the output signal "I" of the photosensor, respectively. Herein, FIG. 18 shows the extinction point and the neighborhood thereof in an enlarged view. When the optical Faraday modulator 88 vibration-modulates the plane of vibration with an amplitude of "δ" and an angular frequency of "ω", "I" is given by the following equation (5):

$$I = T \times I_o \times (\cos[\Theta - \alpha + \delta \times \sin(\omega \times t)])^2 \quad (5),$$

where, "t" is time.

"Θ" is given by the following equation (6):

$$\Theta = \pi/2 + \beta \text{(where, } |\beta| \ll 1\text{)} \quad (6)$$

Substituting this equation (6) into the equation (5) gives the following equation (7):

$$I = T \times I_o \times \{\sin[\beta - \alpha + \delta \times \sin(\omega \times t)]\}^2 \quad (7)$$

When it is assumed that the angle of rotation attributable to the specimen and an amplitude of the modulation are small, that is, $|\alpha| \ll 1$, and $\delta \ll 1$, the equation (7) is approximated by the following equation (8):

$$\begin{aligned} I &\approx T \times I_o \times \{\beta - \alpha + \delta \times \sin(\omega \times t)\}^2 \quad (8) \\ &= T \times I_o \times \{(\beta - \alpha)^2 + 2 \times (\beta - \alpha) \times \delta \times \\ &\quad \sin(\omega \times t) + [\delta \times \sin(\omega \times t)]^2\} \\ &= T \times I_o \times \{(\beta - \alpha)^2 + 2 \times (\beta - \alpha) \times \delta \times \\ &\quad \sin(\omega \times t) + [\delta^2 / 2 \times (1 - \cos(2 \times \omega \times t))]\} \end{aligned}$$

This indicates that the output signal "I" of the photosensor contains signal components of angular frequency equals 0 (DC), "ω" and "2×ω", respectively. This is obvious also from FIG. 18. By the phase sensitive detection of the value "I" with the vibration-modulated signal as a reference signal in the lock-in amplifier, it is possible to pick up the component of the angular frequency "ω", i.e., the value "S" shown by the following equation (9):

$$S = T \times I_o \times 2 \times (\beta - \alpha) \times \delta \quad (9)$$

This "S" equals to zero only when β=α, i.e., at the extinction point. In the process of rotating the analyzer, in other words, sweeping "β", the value of "β" is the angle "α" of rotation when "S" becomes zero.

As described previously, by modulating the direction of polarization, it is possible to pick up the signal of the modulated frequency component selectively while separating the signal from noises attributable to an intensity of the light source, a fluctuation in the power source, a radiation and the like, thereby to derive a signal "S" with high S/N ratio. Therefore, the extinction point can be determined accurately by using this value of "S", and hence highly accurate measurement of the angle "α" of rotation is permitted.

A sample cell for accommodating the specimen used in the above-mentioned polarimeter has a pair of transparent light-transmitting windows which permit the light to transmit through the inside thereof. Heretofore, the sample cells have been configured, for instance, in a box made of glass with its top end open. Liquid specimens are introduced into the cells through the top open end by the use of a pipette, a syringe and the like.

The measurement is performed for every sample cells and the replacement of the specimen is also performed for every sample cells. Namely, the measurement is performed after introducing the specimen into the sample cell and arranging the sample cell in an optical system. The specimen is therefore required to be replaced together with the sample cell. Further, for using the sample cell again, it is required to exhaust the specimen from the sample cell taken out from the optical system and to wash the sample cell. As described previously, the conventional polarimetry consumes much man power.

In addition, when the specimen is dropped into the sample cell, bubbles are liable to be produced in the specimen. Therefore, it has a problem that the bubbles existing in the optical path during the measurement deteriorates the accuracy of the measurement.

BRIEF SUMMARY OF THE INVENTION

An object of the present invention is to provide a sample cell for polarimetry which permits easy replacement of the liquid specimen.

Another object of the present invention is to provide a sample cell capable of preventing mixing of bubbles into the liquid specimen and performing the polarimetry with high accuracy.

The present invention provides a sample cell for polarimetry comprising:

a tubular base member having a cavity which pierces through the member and connects a pair of end faces of the base member for accommodating a specimen, and a pair of flanges provided around the end faces;

a pair of light-transmitting windows for sealing a pair of open ends of the cavity; and a coil configured by winding a wire on the base member between the flanges.

In a preferred mode of the present invention, the sample cell further comprises at least one channel for permitting said cavity to communicate with the outside. Herein, the channel includes an inlet channel for introducing the specimen into the sample cell, an outlet channel for expelling the specimen from the sample cell and a vent hole for permitting a flow of air between the inside and the outside of the sample cell at the time of introducing and expelling the specimen. However, it is not imperative to provide these three kinds of channels, respectively, and a channel which can perform a plurality of the above functions may be provided instead. For instance, one channel can serve both as the inlet channel and the outlet channel. As shown, by providing the channel which communicates the cavity with the outside, the replacement of the specimen and the washing of the inside of the cell are made easy. Preferably, the vent hole is preferentially provided above an optical path of a transmitting light, whereas the channel for introducing or expelling the specimen or the like is provided above the optical path or at the undermost part of the cavity.

In another preferred mode of the present invention, the top face or bottom face of the cavity is inclined with respect to the direction of advance of the transmitting light. By virtue of this, it is possible to move the bubbles produced in the specimen, thereby to remove them from the direction of advance of the transmitting light.

The present invention further provides a polarimetry comprising the steps of:

arranging a sample cell which comprises a tubular base member having a cavity which pierces through the base member and connects a pair of end faces of the base member for accommodating a specimen, and a pair of flanges provided around the end faces, a pair of light-transmitting windows for sealing a pair of open ends of the cavity, and a coil configured by winding a wire on the base member between the flanges, while inclining an axis of the cavity;

introducing a liquid specimen to be measured into the cavity; and projecting a light upon the light-transmitting window along the axis of the cavity.

In a preferred mode of the present invention, channels for communicating the inside of the cavity with the outside thereof are provided at top end and bottom end of the cavity of the sample cell, respectively, and the specimen is introduced into the cavity through the channel at the bottom end. By so designing, bubbles are hardly generated during the introduction of the specimen, and it is possible to move the bubbles produced during the introduction towards the upper end of the cavity more effectively.

If a movement of the bubbles is taken into consideration, the same effect may also be obtained by inclining the sample cell and projecting the light in the horizontal direction. However, in this case, in order to secure an optical path length equivalent to the case of inclining the direction of projecting light, there is a need for enlarging the diameter or the length of the cavity. And hence, a larger amount of specimen is required. By contrast to this, according to the polarimetry of the present invention, it is possible to make the amount of specimen for one measurement small, by inclining also the direction of projecting light.

While the novel features of the invention are set forth particularly in the appended claims, the invention, both as to organization and content, will be better understood and appreciated, along with other objects and features thereof, from the following detailed description taken in conjunction with the drawings.

BRIEF DESCRIPTION OF THE SEVERAL VIEWS OF THE DRAWING

FIG. 1A is a front end view of a sample cell in one embodiment of the present invention, and FIG. 1B is a longitudinal cross-sectional view of the same sample cell.

FIG. 2 is a schematic view for showing a configuration of a polarimeter of the same embodiment.

FIG. 8A is a front end view of a sample cell in a still further embodiment of the present invention, and FIG. 8B is a longitudinal cross-sectional view of the same sample cell.

FIG. 9A is a front end view of a sample cell in a still further embodiment of the present invention, and FIG. 9B is a longitudinal cross-sectional view of the same sample cell.

FIG. 10A is a front end view of a sample cell in a still further embodiment of the present invention, and FIG. 10B is a longitudinal cross-sectional view of the same sample cell.

DETAILED DESCRIPTION OF THE INVENTION

Figure 3:
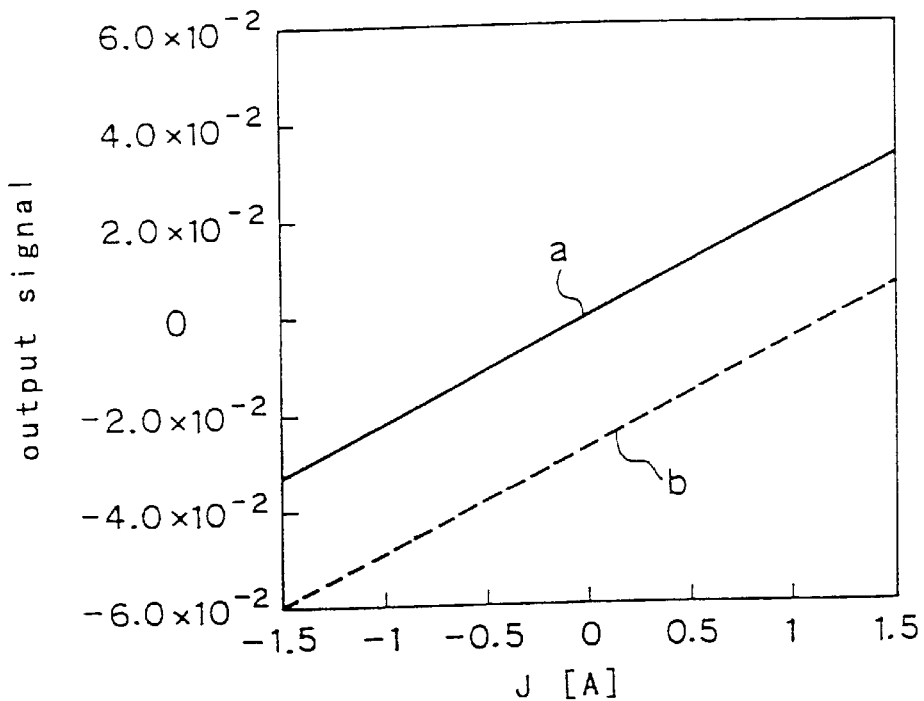
FIG. 3 is a characteristic diagram showing a relationship between a current supplied to a coil of the same polarimeter and the output of a lock-in amplifier.

In the present invention, a tubular sample cell of substantially sealed-type having a cavity is used instead of a box-type sample cell which has been used in the conventional polarimeter. Both the end faces of the cavity is sealed with a light-transmitting material and the specimen is contained in the cavity. A coil is provided around the sample cell for generating a magnetic field inside the cavity.

Not being limited to the case of the optical Faraday modulator configured with flint glass, an optical Faraday effect attributable to the specimen itself is also brought in the case of applying the magnetic field to the specimen accommodated in the cell, for rotating the plane of vibration of the light transmitting through the inside of the cell. By this phenomenon, it is possible to permit the sample cell itself to function as the optical Faraday modulator, and hence a simplification and a miniaturization of the configuration of the polarimeter becomes possible.

The optical Faraday effect can be obtained also in the cases of using water, chloroform, acetone and the like which are widely used as the medium.

Verdet's constants V of the typical media are shown in TABLE 1. In the cases of any media, the Verdet's constant V varies with the kind of the medium, the wavelength of light and the temperature.

TABLE 1

| Medium | V [minute/A] |
| --- | --- |
| Water | $1.645 \times 10^{-2}$ |
| Chloroform | $2.06 \times 10^{-2}$ |
| Acetone | $1.42 \times 10^{-2}$ |
| Quartz | $2.091 \times 10^{-2}$ |
| Flint glass | $4.85 \times 10^{-2}$ | at 20° C. wavelength = 598 nm

Incidentally, means for applying a magnetic field includes a solenoid coil, a permanent magnet or the like which applies a magnetic field along the direction of the advance of light. It is possible to modulate the magnetic field by modulating the current flown through the solenoid coil or by modulating the distance between the permanent magnet and the specimen. By winding the coil directly around the sample cell in particular, it is possible to combine the sample cell and the means for applying the magnetic field into a single unit while making it small and durable at a low cost. In a case of providing a pair of flanges on the both ends of the sample cell, it is possible to secure a space for retainers for the coil and channels for the specimen at these portions.

Such sample cell uses a base member configured by cutting a block of a non-magnetic material such as aluminum.

When an inlet channel for introducing the specimen into the sample cell, an outlet channel for exhausting the specimen from the sample cell and a vent hole are provided on the sample cell, it is possible to perform a replacement of the specimen and washing of the inside of the cell without detaching the sample cell from the optical system.

When the same sample cell is used for a long term or repeatedly without washing or flushing the inside of the cavity, the light transmitting window planes of the sample cell are contaminated and an accurate measurement becomes impossible. In coping with such contamination, a more accurate measurement is made possible by performing a correction in the following manner.

If the contamination is attributable to a substance which does not demonstrate an optical activity, the contamination corresponds to a substantial decrease in the value "T" in the equation (2) and makes the position of the extinct point unclear. Due to this fact, the accuracy of the measurement value is deteriorated. In this case, a ratio of the variance in the value "I" to the variance in the value "Θ" in the equation (3), or a ratio of the value "S" to the value "β" in the equation (9) becomes small. It is therefore possible to derive a value due to the contamination by measuring a reference specimen whose "T" is known and taking the obtained decrease in the value into account. When the value due to the contamination exceeds a certain value, washing or replacement of the sample cell may well be instructed. In the process, it is not imperative to use the reference specimen and the value due to the contamination may alternatively be derived from a result of a measurement conducted by the use of a specimen whose minimum value of "T" is known.

By contrast, if the contamination is attributable to a substance having an optical activity, the position of the extinction point, i.e., the obtained angle of rotation, shifts as much as the displacement in the position. The value "$I_\alpha$" in the equation (3) and the value "S" in the equation (9) also vary. The displacement is an angle of rotation due to the contamination substance and may simply be added to the angle of rotation attributable to the specimen to be determined. For this reason, when a measurement has previously been conducted on a reference specimen whose angle of rotation is known, and a correction is made on the measurement value of the specimen to be determined by the difference between the previous measurement value and the known angle of rotation, it is possible to ignore an error produced by the contamination substance.

According to such corrections, it is possible to conduct a measurement with high accuracy even if the same sample cell is used repeatedly for a long term. It is therefore possible to greatly extend a term set for washing or replacement of the sample cell (for instance, until the transmittance of the light transmitting window decreases to a specified value), and to make the maintenance and management easy.

In a case of using this polarimeter as a urinalysis equipment for household use in particular, its easiness in maintenance and management greatly promotes its popularization.

In the following paragraphs, preferred embodiments of the present invention will be described with reference to the drawings.

EXAMPLE 1

FIG. 1A and FIG. 1B show a sample cell in accordance with this embodiment. The sample cell 1 is obtained in the following manner.

A base member 2 is obtained by cutting a rectangular solid aluminum block.

First, by cutting side faces of an aluminum block having a square cross-section with a side of 25 mm and a length of 55 mm, a cylindrical part with a diameter of 12 mm is formed on the center thereof, while leaving untouched parts with a width of 10 mm on the both ends, thereby to form flanges 2a and 2b. Then, by forming a cylindrical cavity 3 with a diameter of 8 mm which is coaxial with the cylindrical part between the both end faces, the base member 2 is obtained. On both open ends of the cavity 3, shallow holes with a diameter of 12 mm and a depth of 2.5 mm are provided, and glass plates 4 with a diameter of 12 mm and a thickness of 2.5 mm are tightly fitted into the holes, respectively. The cavity 3 has a length i.e., the length of an optical path, of 50 mm and can accommodates a specimen of about 2.5 cc therein.

By winding an enameled wire with a diameter of 0.7 mm around the cylindrical part cut between the flanges 2a and 2b of the base member 2 for 600 turns, a solenoid coil 5 with a length of 35 mm is formed. The solenoid coil 5 is for applying a magnetic field to the specimen accommodated in the cavity 3. As shown, by providing the flanges 2a and 2b, the configuration of the solenoid coil 5 is made easy. Threaded holes 6a and 6b are provided on the flanges 2a and 2b, respectively for fixing the sample cell 1 on a polarimeter. The diameter of the threaded holes 6a and 6b is 3 mm and the depth thereof is 5 mm. Only after providing the flanges 2a and 2b on the base member 2, provision of these threaded holes 6a and 6b becomes possible. With this measure, installation of the sample cell 1 on the polarimeter becomes easy.

An example of the polarimeter which uses the sample cell 1 is shown in FIG. 2. A semiconductor laser projector module 8 projects a semiconductor laser with a wavelength of 780 nm of an elliptical cross section with a long diameter of about 4 mm and a short diameter of about 2 mm in a substantial parallel ray as indicated by the dashed line in the figure. The semiconductor laser projector module 8 also contains a driving circuit for the semiconductor laser which permits the semiconductor laser to oscillate continuously. A polarizer 9 transmits only such specified polarized component of the projected semiconductor laser that has a plane of vibration which is, for instance, parallel to the plane of this paper. An analyzer 10 is arranged so as to transmits only such a polarized component of the light transmitted through the sample cell 1 that is perpendicular to the axis of transmission of the polarizer 9. The photosensor 11 detects the light transmitted through the analyzer 10. All of these components are fixed on a rail-shaped base plate 7 having a length of 150 mm.

A current source 12 can supply a sweep current of from −5 A to +5 A to the solenoid coil 5 on an instruction signal from a computer 13. The computer 13 also records and analyzes an output signal from a lock-in amplifier 15. A signal generator 14 supplies a modulation signal to the current source 12 for modulating the current to be supplied to the solenoid coil 5 of the sample cell 1. The current source 12 interposes the modulation current due to the modulation signal in the sweep current instructed by the computer 13, and supplies the interposed current to the solenoid coil 5. In this embodiment, the current source 12 supplies the modulation current with an amplitude=0.02 A to the solenoid coil 5 based on the modulation signal of 1.3 kHz. The lock-in amplifier 15 performs a phase sensitive detection on the output signal of the photosensor 11 by taking the modulation signal of the signal generator 14 as a reference signal. The output signal of the lock-in amplifier 15 corresponds to the component of the angular frequency "ω" of the output signal of the photosensor 15 in the equation (8) i.e., the value "S" in the equation (9). Therefore, a time point when "S" equals to zero is in the extinction point.

FIG. 3 shows the output signal of the lock-in amplifier 15, when the current to be supplied to the coil 5 is swept in a range between −1.5 A and +1.5 A. In FIG. 3, the abscissa indicates the current "J" to be supplied to the coil 5 and the ordinate represents the output signal (arbitrary value) of the lock-in amplifier 15.

In the figure, the solid line "a" represents the case wherein pure water which does not demonstrate an optical activity is measured as the specimen. In this case, when "J" equals to zero i.e., any magnetic field is not applied to the pure water as the specimen, an extinction point appears. When "J" is allowed to vary, the plane of vibration of the light rotates due to the optical Faraday effect and the output signal "S" of the lock-in amplifier 15 varies as in the case of varying p in the equation (6) i.e., of rotating the analyzer 10.

In contrast to this, the dashed line "b" in FIG. 3 indicates the case of using a sucrose aqueous solution with a concentration of 250 mg/dl at 20° C. as the specimen. In this case, an extinction point appears at J=1.21 A. Namely, the dashed line "b" coincides to a straight line obtained by parallelly shifting the solid line "a" along the abscissa by +1.21 A. The width of this shift of the extinction point corresponds to the angle of rotation due to the specimen.

In the following description, the above-mentioned fact will be confirmed quantitatively.

On the basis of the equation (1), the angle of rotation "α" attributable to the sucrose in the specimen is:

$$\alpha = [\alpha]/10000 \times 0.05 \times 250 \approx 0.0831 [\text{degree}].$$

Next, when an angle of rotation in the direction of polarization due to the optical Faraday effect "a" is calculated by the use of the equation (4), the following result is obtained.

Based on the characteristics of the solenoid coil 5, it is derived that the magnetic field H=6.05×103 A/m under the condition of J=1.21 A. From this value and the Verdet's constant "V" of water shown in TABLE 1, $$a = 1.645 \times 10^{-2} \times 0.05 \times 10^4 \times 0.05 \approx 4.976 [\text{minute}] = 0.083 [\text{degree}]$$

is derived.

As described above, it is confirmed that the angle of rotation due to the specimen coincides with the angle of rotation due to the optical Faraday effect.

Figure 4:
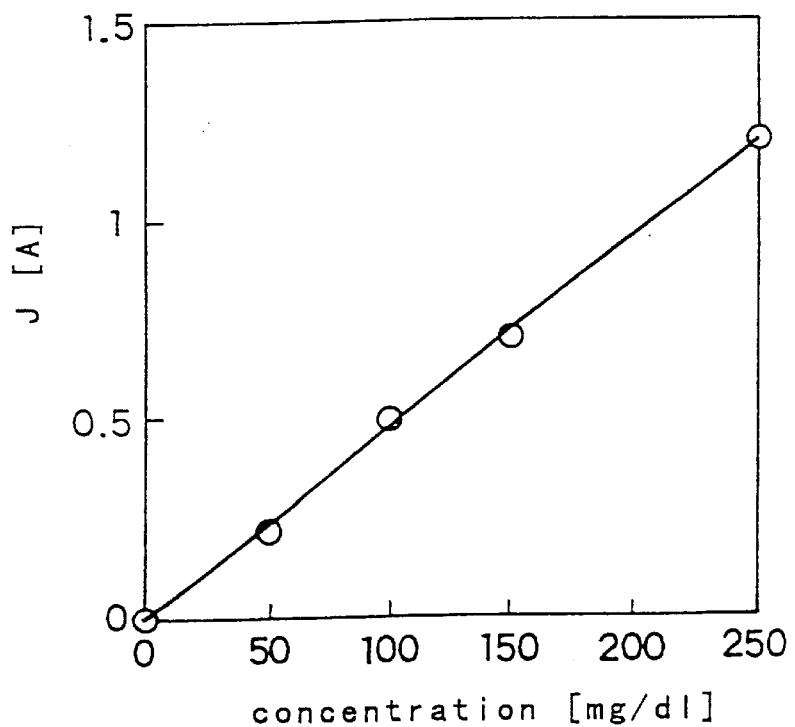
FIG. 4 is a characteristic diagram showing a relationship between a concentration of sucrose aqueous solution and a current supplied to the coil when an extinction point is reached.

In a manner similar to the above, the angles of rotation are additionally measured at 20° C. by using sucrose aqueous solutions with concentrations of 50, 100, 150 and 250 mg/dl, respectively. The results thereof are shown in FIG. 4. In FIG. 4, the abscissa represents the concentration of the sucrose and the ordinate represents the current "J" for reaching the extinction point. As seen from FIG. 4, it is recognized that the one is proportional to the other.

Although such a case where the extinction point exists in the range of sweeping the magnetic field is shown in this embodiment, the angle of rotation can also be calculated, even in another case where no extinction point exists in the range of sweeping, by extrapolating the characteristic in the range, because the output signal "S" of the lock-in amplifier 15 varies linearly with respect to the magnetic field i.e., the current "J", as illustrated by FIG. 3 and indicated by the equation (9). In addition, since "J" and "S" are in a proportional relationship, it is not imperative to sweep the magnetic field continuously but the angle of rotation can instead be calculated by interpolating or extrapolating the results of the measurements on at least two points. By this procedure, it is also possible to shorten the time for conducting the measurement.

Next, a similar measurement is conducted on pure water as the specimen by using a sample cell whose transmitting windows are contaminated as a result of being stood for a long term without washing. In that case, an extinction point appears at J=0.02 A. From this value, the angle of rotation "d" attributable to the contaminating substance on the light transmitting windows of the sample cell is derived on the basis of the equation (4) and TABLE 1 as:

$$d = 1.645 \times 10^{-2} \times 10^2 \times 0.05 \approx 0.082 [\text{minute}] \approx 1.4 \times 10^{-3} [\text{degree}].$$

In a case of measuring the angle of rotation attributable to a fresh specimen by the use of this sample cell, an accurate angle of rotation can be obtained by correcting the measurement value by subtracting "d" from it. Namely, even in such a case of using the same sample cell repeatedly for a long term, it is possible to perform a measurement with high accuracy by correcting the measurement value of the specimen with a measurement value of a reference sample whose angle of rotation is known. By this procedure, it is possible to extend the time period set for washing or replacement of the sample cell until the transmittance of the light transmitting windows decreases to a specified value.

Further, by sweeping the magnetic field i.e., varying the magnetic field from a specified intensity to another specified intensity (including a change of polarity in the magnetic field), it is possible to continuously rotate the plane of vibration of light. By this procedure, it is possible to obtain an effect which is the same as the rotation of the analyzer. Therefore, by placing the polarizer and the analyzer in an orthogonal Nicol's state, in other words, maintaining the relative angle formed between the transmission axes of the both at 90 degrees, it is possible to negate the optical rotation attributable to the optical active substance in the specimen by sweeping the intensity of the magnetic field generated in the specimen, thereby to calculate the angle of rotation based on the intensity of the magnetic field at that time.

In other words, it is possible to measure the angle of rotation by reading out the current value supplied to the coil at an appearance of an extinction point, and by converting it into the intensity of the magnetic field and further into the angle of rotation attributable to the optical Faraday effect. According to this procedure, the angle of rotation can be derived based substantially on the intensity of the magnetic field at the time when the angle of rotation produced by the optical active substance in the specimen coincides to the angle of rotation in the plane of vibration due to the optical Faraday effect.

As described above, according to this embodiment, it is possible to apply a magnetic field to the specimen by winding a coil directly around the sample cell.

EXAMPLE 2

Figure 5A:
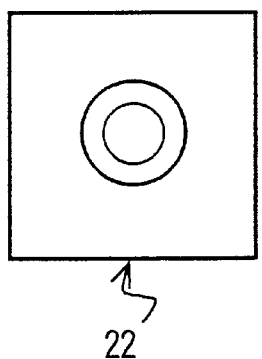
FIG. 5A is a front end view of a sample cell in another embodiment of the present invention.
Figure 5B:
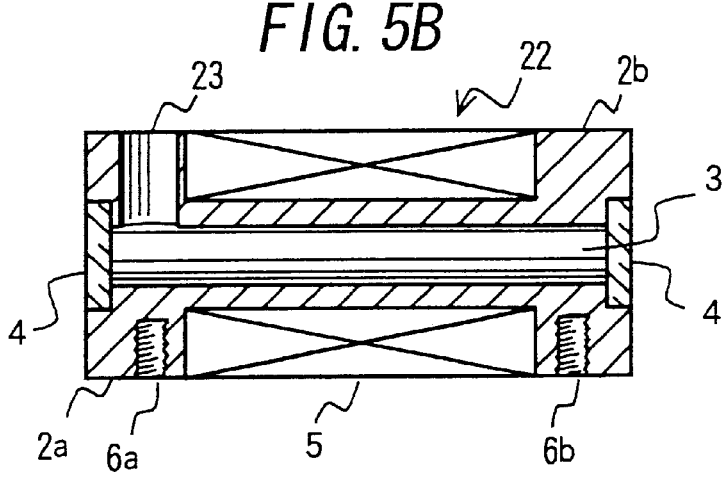
FIG. 5B is a longitudinal cross-sectional view of the same sample cell.

A sample cell in accordance with this embodiment is shown by FIG. 5A and FIG. 5B.

The sample cell 22 has the same structure as that used in EXAMPLE 1. An inlet/outlet channel 23 with a diameter of 6 mm is however provided on the sample cell 22, for communicating the inside of the cavity 3 with the outside. The inlet/outlet channel 23 is arranged above the cavity 3, in particular, so that it is positioned at an upper side of the optical path for the projected light.

The specimen is introduced into the cavity 3 through the inlet/outlet channel 23. At the time of the introduction, air inside the sample cell 22 is expelled therefrom through the inlet/outlet channel 23 to the outside. Herein, since the inlet/outlet channel 23 is formed above the optical path, no air remains in the optical path of light after the introduction of the specimen. Therefore, an accurate measurement is made possible.

The specimen is expelled therefrom by being suctioned through the inlet/outlet channel 23. At the time of washing the cavity 3 of the sample cell 22, water or a cleaning solution is introduced into the cavity 3 through the inlet/outlet channel 23.

By providing the inlet/outlet channel 23 on the sample cell 22 as in this embodiment, replacement of the specimen or washing of the sample cell becomes easy.

EXAMPLE 3

Figure 6A:
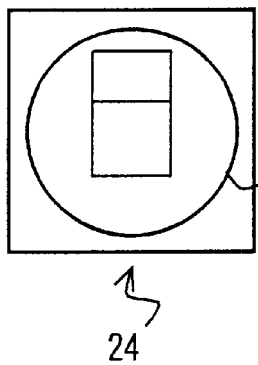
FIG. 6A is a front end view of a sample cell in still other embodiment of the present invention.
Figure 6B:
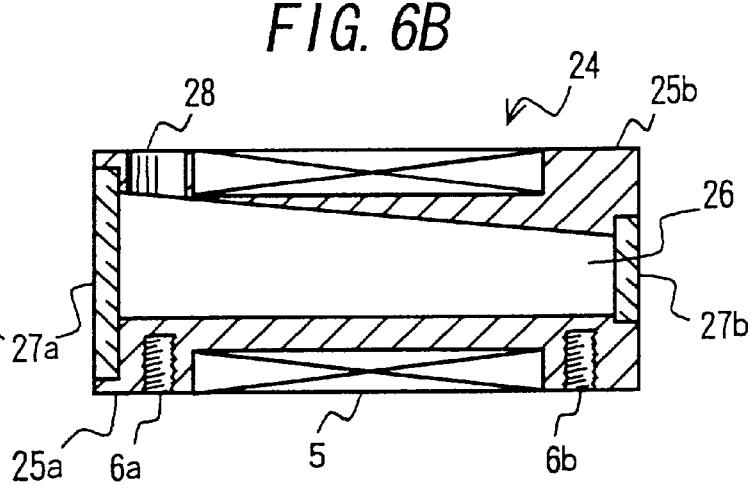
FIG. 6B is a longitudinal cross-sectional view of the same sample cell.

A sample cell in accordance with this embodiment is shown by FIG. 6A and FIG. 6B.

The sample cell 24 of this embodiment is obtained in the following manner.

First, by cutting side faces of an aluminum block having a square cross-section with a side of 25 mm and a length of 55 mm, a cylindrical part with a diameter of 17 mm is formed on the center thereof, while leaving untouched parts with a width of 10 mm on its both ends, respectively, thereby to form flanges 25a and 25b. Then, a cavity 26 having a rectangular cross-section is formed between the both end faces. The cross-section of one open end of the cavity 26 is a rectangle of 8 mm×13 mm and the cross-section of the other open end is a square of 8 mm×8 mm. The top face of the cavity 26 has an inclination of about 5.7 degrees ($\tan^{-1}$ (5/50)) between the both open ends. On the wider open end of the cavity 26, a circular hole with a diameter of 22 mm and a depth of 2.5 mm is provided, and a glass plate 27a with a diameter of 22 mm and a thickness of 2.5 mm is tightly fitted into the hole. On the narrower open end of the cavity 26, a circular hole with a diameter of 12 mm and a depth of 2.5 mm is provided, and a glass plate 27b with a diameter of 12 mm and a thickness of 2.5 mm is tightly fitted into the hole.

On the upper end of the cavity 26 i.e., the wider open end side of the inclined top face of the cavity 26, an inlet/outlet channel 28 having a circular cross section with a diameter of 6 mm is provided.

The length of the optical path of the sample cell 24 thus obtained is 50 mm and the cavity 26 thereof can accommodate a specimen of about 4.2 cc.

The specimen is introduced into the cavity 26 through the inlet/outlet channel 28. At the time of the introduction, air inside the cavity 26 is expelled therefrom through the inlet/outlet channel 28 to the outside. Herein, since the inlet/outlet channel 28 is provided above an optical path, no air remains in the optical path after the introduction of the specimen.

In addition, since the top face of the cavity 26 is inclined and the inlet/outlet channel 28 is provided at the uppermost part thereof, bubbles produced during the introduction of the specimen, after floating themselves upwards, move along the inclined top face up to the inlet/outlet channel 28. Namely, it is possible to prevent the disturbance on a transmitting light by the bubbles mixed with the specimen in the cavity 26. Therefore, a measurement on the angle of rotation can be conducted more accurately as compared with the sample cell 22 of EXAMPLE 2. The specimen introduced into the cavity 26 is expelled therefrom by being suctioned through the inlet/outlet channel 28. At the time of washing the cavity 26, water or a cleaning solution is introduced therein through the inlet/outlet channel 28.

EXAMPLE 4

Figure 7A:
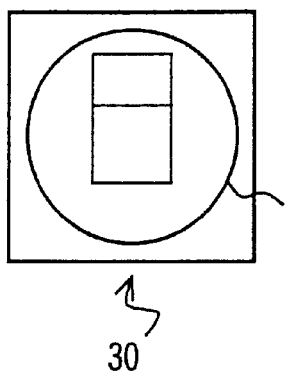
FIG. 7A is a front end view of a sample cell in a further embodiment of the present invention.
Figure 7B:
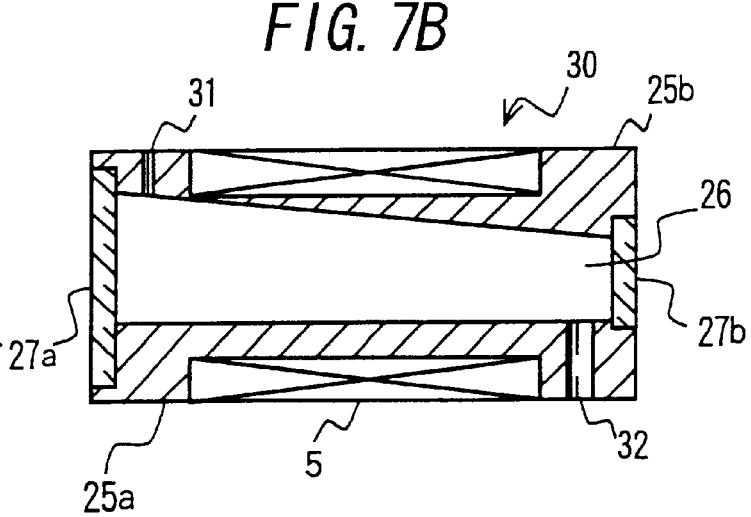
FIG. 7B is a longitudinal cross-sectional view of the same sample cell.

A sample cell in accordance with this embodiment is shown by FIG. 7A and FIG. 7B.

The sample cell 30 has a structure similar to the sample cell 24 used in EXAMPLE 3. However, the sample cell 30 has a vent hole 31 having a circular cross-section with a diameter of 1.0 mm provided on the uppermost part i.e., the wider open end side of the inclined top face of the cavity 26 for communicating the inside with the outside, instead of the inlet/outlet channel 28. On the bottom face at the narrower open end side i.e., the undermost part of the cavity 26, an inlet/outlet channel 32 of a circular cross-section with a diameter of 2.5 mm is arranged. The specimen is introduced into the cavity 26 through the inlet/outlet channel 32. At the introduction, air inside the cavity 26 is expelled therefrom through the vent hole 31. After the measurement, the specimen is expelled therefrom through the inlet/outlet channel 32. At that time, air flows into the cavity 26 through the vent hole 31. At the time of washing the cavity 26, water or a cleaning solution is introduced and expelled through the inlet/outlet channel 32.

In the case of the sample cell of this embodiment, by virtue of providing the inlet/outlet channel 32 at the undermost part of the cavity 26, the expelling of the specimen becomes more easy as compared with the sample cell 24 of EXAMPLE 3. In addition, it is possible to suppress a mixing the specimen introduced into the cavity 26 with air, and to greatly reduce the amount of the bubbles produced during the introduction of the specimen.

EXAMPLE 5

A sample cell in accordance with this embodiment is shown by FIG. 8A and FIG. 8B.

The sample cell 34 uses a base member 35 configured by working on an aluminum block similar to those in the above-mentioned embodiments, in which an axis of the cylindrical cavity 36 is inclined. The sample cell 34 is produced in the following manner.

First, by cutting side faces of an aluminum block, a cylindrical part with a diameter of 17 mm is formed on the center thereof, while leaving untouched parts with a width of 10 mm on the both ends, thereby to form flanges 35a and 35b. Then, a cylindrical cavity 36 having a diameter of 12 mm and an axis inclined by about 5.7 degrees ($\tan^{-1}$ (5/50)) with respect to the axis of the cylindrical part is provided between the both end faces. On both open ends of the cavity 36, holes with a diameter of 22 mm and a depth of 2.5 mm are provided, and glass plates 37a and 37b with a diameter of 22 mm and a thickness of 2.5 mm are tightly fitted into the holes, respectively. The cavity 36 has a length i.e., length of the optical path of 50 mm and can contain the specimen of about 5.7 cc.

The sample cell 34 has a vent hole 38 having a circular cross-section with a diameter of 1.0 mm provided on the uppermost part of the cavity 36 for communicating the inside with the outside. In addition, an inlet/outlet channel 39 having a circular cross-section with a diameter of 2.5 mm is provided at the undermost part of the cavity 36.

By virtue of providing an inclination on the bottom face of the cavity 36 for containing the specimen as in the sample cell 34 of this embodiment, the expelling of the specimen becomes more easy as compared with the sample cell 30 of EXAMPLE 4.

EXAMPLE 6

A sample cell in accordance with this embodiment is shown by FIG. 9A and FIG. 9B.

The sample cell 41 has a structure similar to the sample cell 24 used in EXAMPLE 3. The sample cell 41 however has an outlet/vent hole 42 of a circular cross-section with a diameter of 2.5 mm provided, instead of the inlet/outlet channel 28. In addition, at the narrower open end side of the bottom face of the cavity 26, an inlet channel 43 of a circular cross-section with a diameter of 2.5 mm is provided.

At the time of replacing the specimen, a fresh specimen is introduced into the cavity 26 through the inlet channel 43, and the used specimen is expelled therefrom by being pushed out through the outlet/vent hole 42. At the time of washing the cavity 26, water or a cleaning solution is continuously introduced through the inlet channel 43 and expelled through the outlet/vent hole 42.

EXAMPLE 7

A sample cell in accordance with this embodiment is shown by FIG. 10A and FIG. 10B.

The sample cell 45 has a structure similar to the sample cell 34 used in Embodiment 5. However, the sample cell 45 has an inlet/vent hole 46 of a circular cross-section with a diameter of 2.5 mm provided, instead of the vent hole 38. An outlet channel 47 having a similar configuration to that of the inlet/outlet channel 39 is used exclusively for expelling the specimen from the cavity 36. The specimen is introduced into the cavity through the inlet/vent hole 46.

At the same time, air inside the cavity 36 is expelled therefrom through the inlet/vent hole 46. At the time of replacing the specimen, a fresh specimen to be determined is introduced into the cavity 36 through the inlet/vent hole 46, while the already-examined specimen is remaining in the cavity 36, and the examined specimen which had previously been introduced into the cavity 36 is expelled through the outlet channel 47. At the time of washing the cavity 36, water or a cleaning solution is introduced therein through the inlet/vent hole 46 and expelled through the outlet channel 47.

As mentioned above, by designing the base member so as to introduce the fresh specimen into the cavity from the top thereof, and to expel the examined specimen in the cavity from the bottom thereof, both the specimens are rendered hardly liable to mix with each other, and the replacement of the specimen in the cavity becomes easy. For the same reason, the washing of the cavity is made easy.

EXAMPLE 8

Figure 11A:
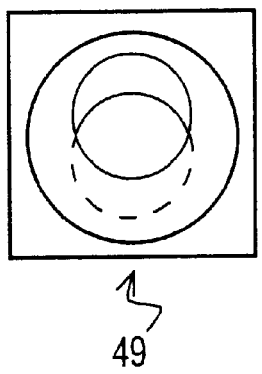
FIG. 11A is a front end view of a sample cell in a still further embodiment of the present invention.
Figure 11B:
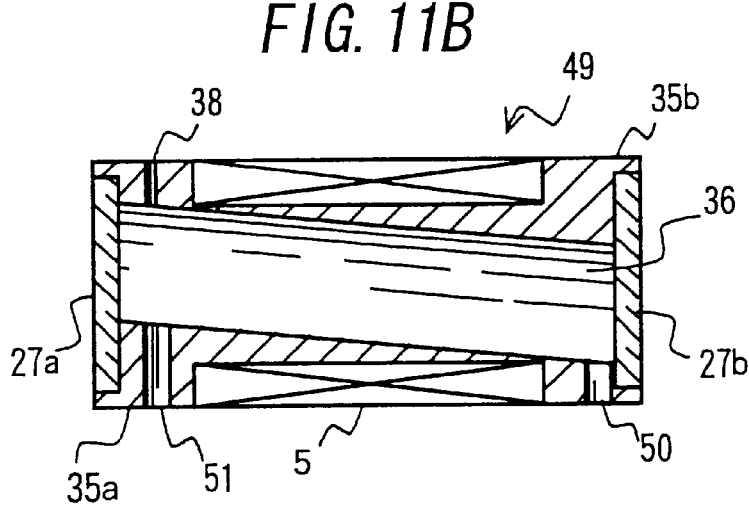
FIG. 11B is a longitudinal cross-sectional view of the same sample cell.

A sample cell in accordance with this embodiment is shown by FIG. 11A and FIG. 11B.

The sample cell 49 has a structure similar to the sample cell 34 used in EXAMPLE 5. However, the sample cell 49 has an inlet channel 51 is additionally provided on the bottom of the cavity 36 at a position opposite to the vent hole 38. In addition, an outlet channel 50 having a similar configuration to that of the inlet/outlet channel 39 is used exclusively for expelling the specimen.

A specimen to be examined is supplied to the cavity 36 through the inlet channel 51. Air inside the cavity 36 is expelled therefrom through the vent hole 38. As shown, by the virtue of inclining the axis of the cylindrical cavity 36, even in a case of involving the bubbles in the cavity 36, the bubbles do not interfere with the transmitting light because the bubbles move along the wall of the cavity 36.

In addition, by providing the inlet channel 51 on the bottom, it is possible to suppress a mixing of the air inside the cavity 36 with the specimen at the time of introducing the specimen, and to greatly reduce the bubbling. The specimen in the cavity 36 is expelled therefrom through the outlet channel 50. At that time, air is flown into the cavity 36 through the vent hole 38. By virtue of inclining the axis of the cylindrical cavity 36, the expelling is easy. At the time of replacing the specimen, a fresh specimen is introduced into the cavity 36 through the inlet channel 51, and the examined specimen which had previously been introduced into the cavity 36 is expelled through the outlet channel 50 by being pushed out. At the time of washing the cavity 36, water or a cleaning solution is introduced therein through the inlet channel 51 and expelled therefrom through the outlet channel 50.

EXAMPLE 9

Figure 12A:
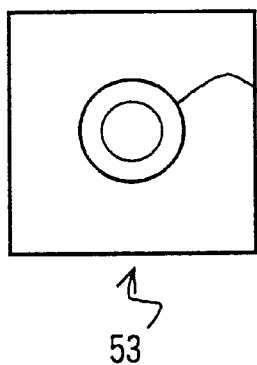
FIG. 12A is a front end view of a sample cell in a still further embodiment of the present invention.
Figure 12B:
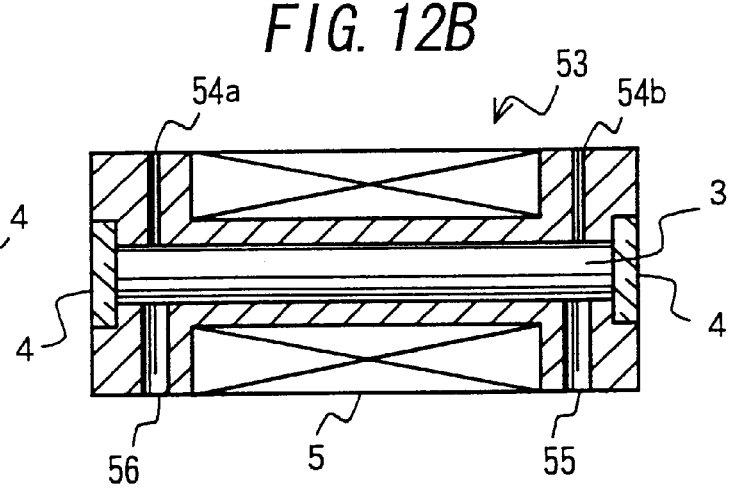
FIG. 12B is a longitudinal cross-sectional view of the same sample cell.

A sample cell in accordance with this embodiment is shown by FIG. 12A and FIG. 12B.

The sample cell 53 has the same structure as that used in EXAMPLE 1. However, a vent hole 54a having a circular cross-section with a diameter of 1.0 mm is provided on the top of the cavity 3 at the one open end side. On the top of the cavity 3 at the other open end side, another vent hole 54b is provided. In addition, on the bottom of the cavity at its both open ends side, an inlet channel 55 having a circular cross-section with a diameter of 2.5 mm and an outlet channel 56 having a circular cross-section with a diameter of 2.5 mm are provided, respectively.

By virtue of providing the inlet channel 55 on the bottom as shown, it is possible to greatly reduce the bubbling at the introduction of specimen. When the examined specimen is expelled therefrom through the outlet channel 56, air is flown into the cavity 3 through the vent holes 54a and 54b.

At the time of replacing the specimen, a fresh specimen is introduced through the inlet channel 55 and the examined specimen is expelled therefrom by being pushed out through the outlet channel 56. At the time of washing the cavity 3, water or cleaning solution is introduced therein through the inlet channel 55.

EXAMPLE 10

By virtue of inclining the top or bottom face of the cavity in the sample cell or inclining the axis of the cylindrical cavity as mentioned in the foregoing embodiments, it is possible to suppress the bubbling at the introduction of specimen. However, the working on the cavity to have such peculiar configurations represents a low productivity. In addition, the cavity of the peculiar configuration needs a large amount of specimen. For instance, the sample cell 34 of Embodiment 5 shown in FIG. 8A and FIG. 8B requires a larger diameter of the cylindrical cavity 36 for securing an equivalent optical path length as that of the sample cell 1 shown in FIG. 1A and FIG. 1B.

Under the circumstances, a method of performing polarimetry on a smaller amount of the specimen by the use of a sample cell similar to the sample cell 1 of EXAMPLE 1 which is excellent in its workability will be described in this embodiment.

Figure 13:
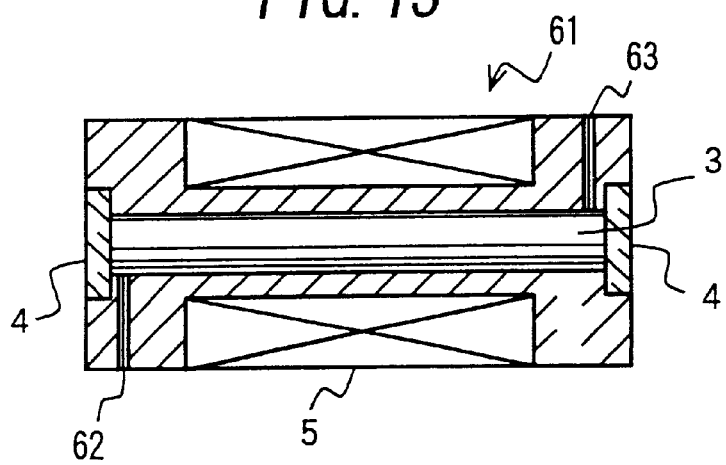
FIG. 13 is a longitudinal cross-sectional view of a sample cell in a still further embodiment of the present invention.

The sample cell 61 shown in FIG. 13 has a structure similar to the sample cell 1 of EXAMPLE 1.

On one open end of the cavity 3 of the sample cell 61, an inlet/outlet channel 62 with a diameter of 1.0 mm which communicates with the outer side wall is arranged. On the other open end of the cavity 3 and at a position axially-rotated by 180 degree with respect to the position where the inlet/outlet channel 62 is arranged, a vent hole 63 with the same diameter of 1.0 mm which also communicates with the outer side wall is arranged.

Figure 14:
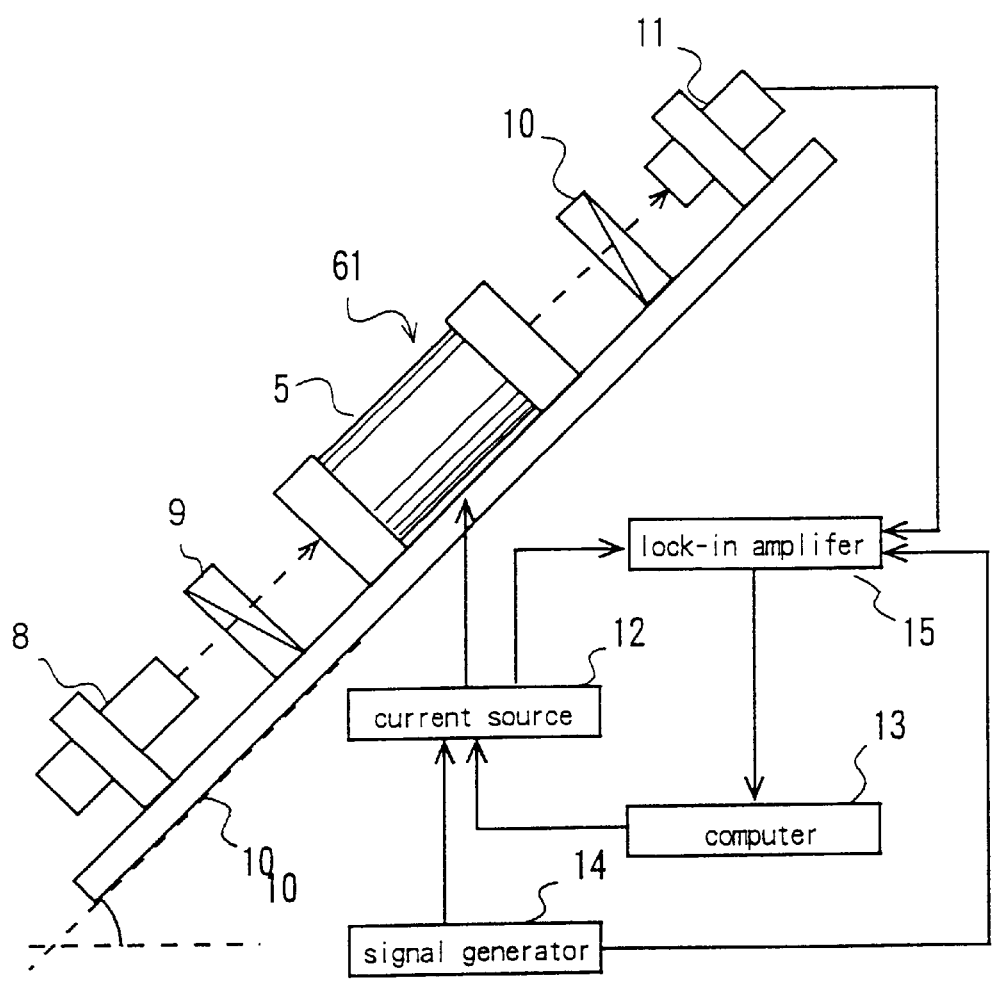
FIG. 14 is a schematic view for showing the configuration of a polarimeter of the same embodiment.
Figure 15:
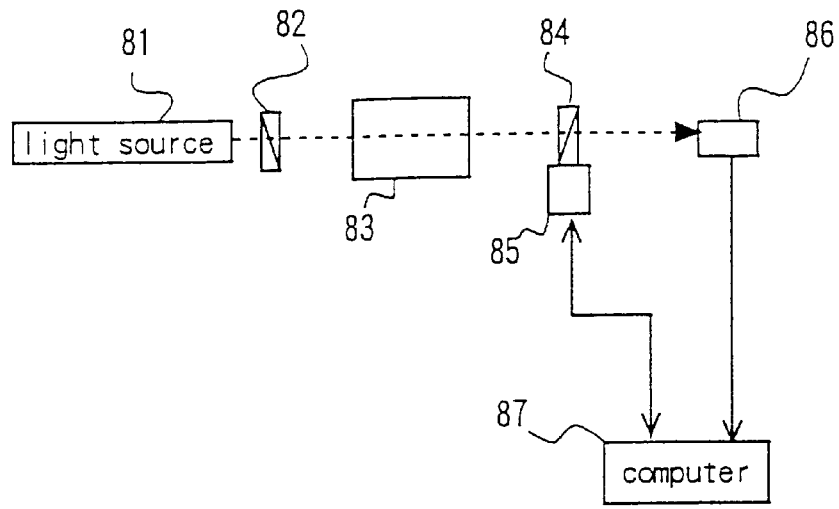
FIG. 15 is a schematic view for showing the configuration of a conventional polarimeter.
Figure 16:
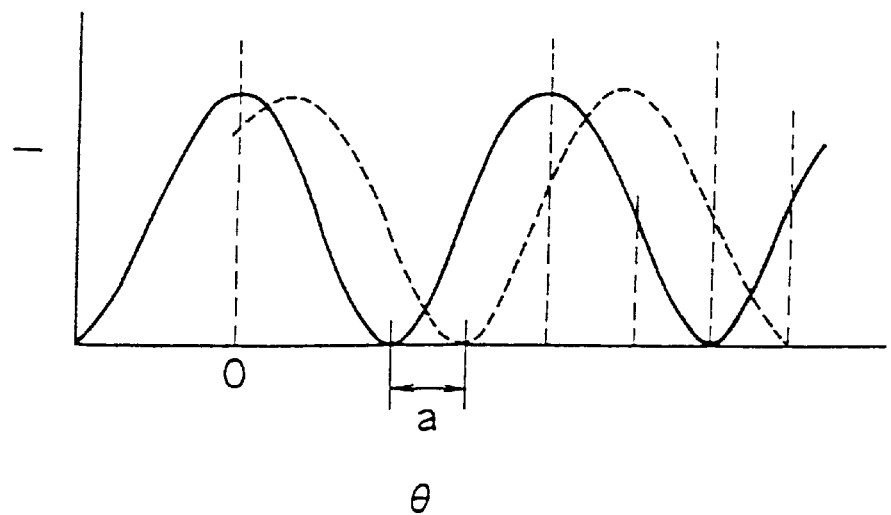
FIG. 16 is a characteristic diagram showing a relationship between an angle of rotation of an analyzer in the polarimeter and an intensity of a light transmitting through the analyzer.
Figure 17:
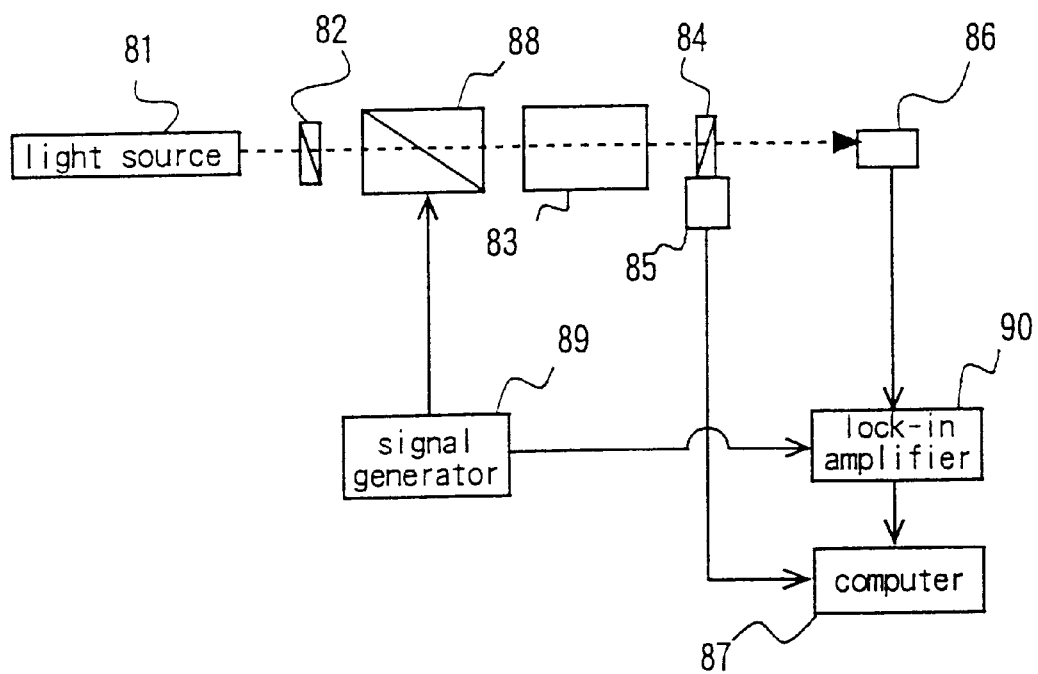
FIG. 17 is a schematic view for showing a configuration of another conventional polarimeter.
Figure 18:
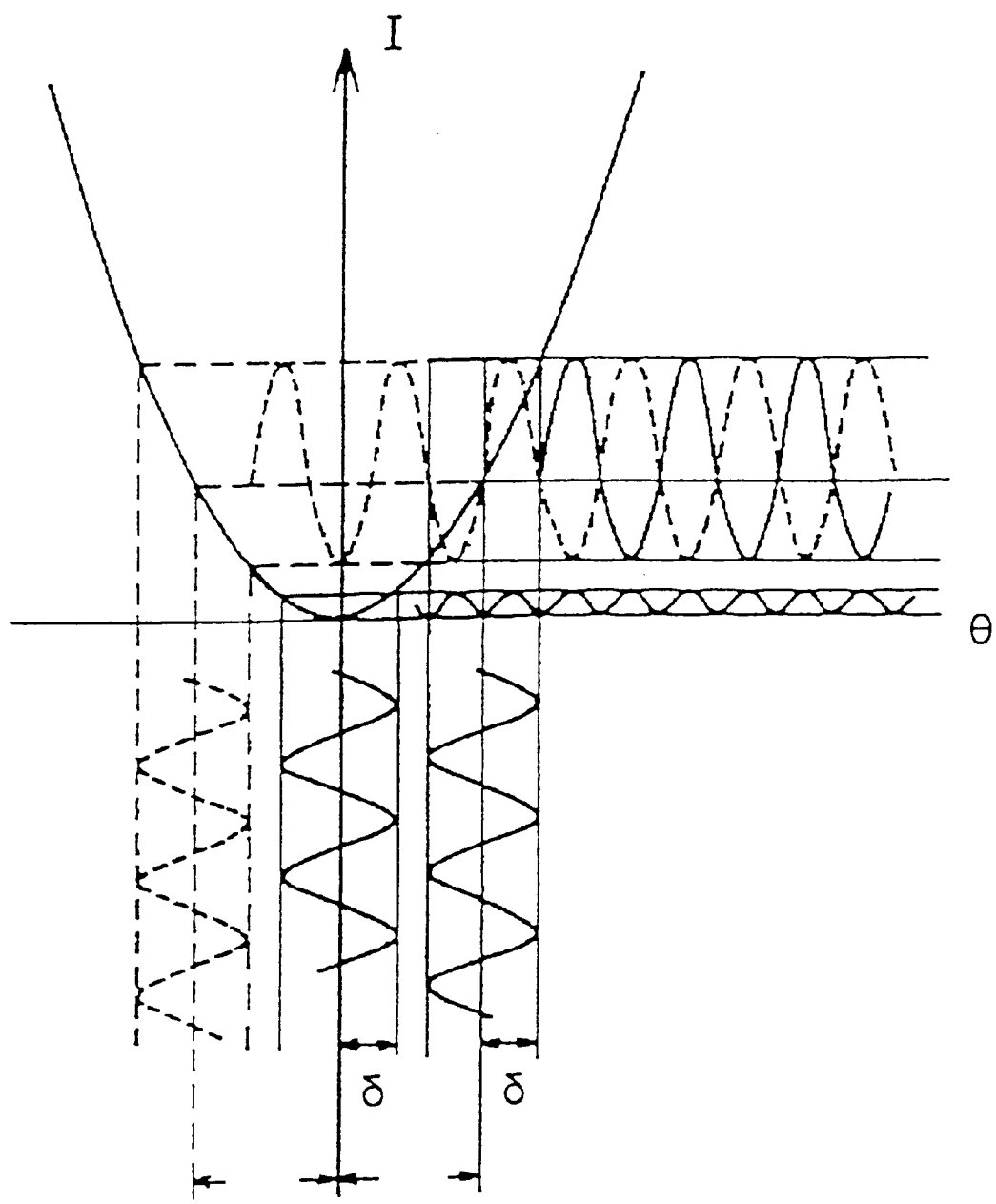
FIG. 18 is a characteristic diagram showing the relationship between the current supplied to a coil and an output of an lock-in amplifier in the polarimeter.

The sample cell 61 is used in a manner as shown, for instance, in FIG. 14.

As shown, by using a polarimeter similar to that in EXAMPLE 1, the axis of the sample cell i.e., the direction of the advance of the transmitting light is inclined at an angle, for example, 45 degrees.

The sample cell 61 is arranged so that the inlet/outlet channel 62 is placed at its lower end and its vent hole 63 is placed at its upper end.

At the time of introducing a specimen to be examined, the specimen is introduced into the sample cell 61 through the inlet/outlet channel 62 by using a syringe, a pump or the like. At that time, since air inside the cavity 3 is expelled through the vent hole 63, it is possible to introduce a liquid specimen smoothly. Herein, since the top face of the cavity 3 is inclined, bubbles are hard to generate during the introduction of the specimen, and since the generated bubbles move, after floating themselves upwards in the specimen, towards the upper end of the cavity along the top face of the cavity 3, the bubbles do not interfere with the transmission of the projected light.

When the specimen is replaced after one measurement, the examined specimen in the cavity 3 is expelled therefrom through the inlet/outlet channel 62.

In a case wherein the amount of specimen for the measurement is larger than the volume of the cavity, a fresh specimen may be introduced through the inlet/outlet channel 62 in a state where the specimen which had previously been measured remains in the cavity.

At the time of washing the sample cell 61, water or a cleaning solution is likewise introduced into the cavity through the inlet/outlet channel 62. By introducing a larger amount of cleaning solution or the like than the volume of the cavity 3 through the inlet/outlet channel 62, thereby to supply the cleaning solution continuously to the cavity 3 and to expel it through the vent channel 63, it becomes possible to wash the sample cell 61 effectively.

In this embodiment, although the light is illustrated to be projected upwards from the bottom, a similar technical advantage will be obtained by projecting the light downwards from the top.

With respect to the suppression of the bubbling in the specimen, a similar technical advantage is obtained in the case of measuring by using the sample cell 34 of EXAMPLE 5 and projecting the light in the horizontal direction. However, in order to prevent the refraction of the incident light on the specimen, the glass plate 37a for the light transmitting plane should be placed in perpendicular to the incident direction of the light. Therefore, in the case of inclining the axis of the cavity 36 of the sample cell 34, there is a need for elongating the length of the cavity 36 for securing an optical path length as that of the sample cell 61 used in this embodiment.

In addition, in a case of inclining the axis of the cavity 36 at a larger angle, there is a need for enlarging the cross-sectional area of the cavity 36. Therefore, a larger amount of the specimen is required as compared with the sample cell 61 of this embodiment. Further, since there is another need for inclining the normal of the transmitting plane with respect to the axis of the cavity 36, the workability of the sample cell is poor.

In a case of applying a magnetic field to the specimen in the sample cell 34 by the coil as in the case of the sample cell 61 of this embodiment, there is a need for increasing the turn number of the coil 5 or the current value to be supplied to the coil 5 for generating a magnetic field equivalent to that for the sample cell 61 because the sample cell 34 has a cavity 26 of larger diameter or length. If the turn number of the coil 5 is increased, a heat generated in the coil 5 increases. When the current value to be supplied to the coil 5 is increased, the heat generated in the coil 5 increases and the preciseness in the measurement is made inferior.

As described previously, according to the present invention, the measurement on the optical characteristic of the specimen can be conducted with a high operability because there is no requirement of detachment of sample cell at the measurement of the optical characteristic. In addition, since it is possible to suppress the adverse effect of the bubbles produced during the introduction of the specimen, a polarimetry with high precision is made possible. Further, it is possible to reduce the amount required for the measurement.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

We claim:

1. A sample cell for polarimetry comprising:
   a tubular base member having a cavity which pierces through said base member and connects a pair of end faces of said base member for accommodating a specimen to be examined, and a pair of flanges provided around said end faces;

a pair of light-transmitting windows for sealing a pair of open ends of said cavity;

a coil configured by winding wire on said base member between said flanges, said coil having a width which is narrower than the length of said cavity, and at least one channel for permitting said cavity to communicate with the outside, said channel being provided above an optical path of light transmitting through said cavity.

2. The sample cell for polarimetry in accordance with claim 1, wherein said channel comprises an inlet/outlet channel for introducing and expelling said specimen.

3. The sample cell for polarimetry in accordance with claim 2, wherein said channel further comprises a vent hole for permitting a flow of air between said cavity and the outside thereof.

4. The sample cell for polarimetry in accordance with claim 1, wherein said channel comprises an outlet/vent hole for expelling said specimen and for permitting a flow of air.

5. The sample cell for polarimetry in accordance with claim 4, wherein said outlet/vent hole is provided above an optical path of a light transmitting through said cavity.

6. The sample cell for polarimetry in accordance with claim 1, wherein said channel comprises an inlet channel for introducing said specimen and an outlet channel for expelling said specimen.

7. The sample cell for polarimetry in accordance with claim 1, wherein said channel comprises: an inlet channel for introducing said specimen, an outlet channel for expelling said specimen and a vent hole for communicating air between said cavity and the outside thereof.

8. The sample cell for polarimetry in accordance with claim 7, wherein said outlet channel and vent hole are provided above an optical path of a light transmitting through said cavity.

9. A polarimetry comprising the steps of:

arranging a sample cell which comprises; a tubular base member having a cavity which pierces through said base member and connects a pair of end faces of said base member, for accommodating a specimen to be examined, and a pair of flanges provided around said end faces, a pair of light-transmitting windows for sealing a pair of open ends of said cavity, at least one channel for permitting said cavity to communicate with the outside, said channel being provided above an optical path of light transmitting through said cavity and a coil configured by winding a wire on said base member between said flanges, while inclining an axis of said cavity;

introducing a liquid specimen into said cavity; and projecting a light upon said light-transmitting window along the axis of said cavity.

10. A sample cell for polarimetry comprising:

a tubular base member having a cavity which pierces through said base member and connects a pair of end faces of said base member for accommodating a specimen to be examined, and a pair of flanges provided around said end faces;

a pair of light-transmitting windows for sealing a pair of open ends of said cavity;

a coil configured by winding wire on said base member between said flanges; and a channel located at an undermost portion of said cavity, relative to a direction of buoyancy of bubbles passing through a specimen contained within said cavity, wherein said channel reduces bubbles which adversely effect polarimetry measurements of said specimen upon insertion into said cavity.

11. The sample cell of claim 10, further comprising a lowermost cavity barrier and an uppermost cavity barrier, wherein said uppermost cavity barrier is non-parallel to said lowermost cavity barrier forming a narrow end, and wherein said channel is located substantially adjacent to said narrow end.

12. The sample cell of claim 10, further comprising a lowermost cavity barrier and an uppermost cavity barrier, wherein both said lowermost and uppermost cavity barriers are non-perpendicular to said direction of buoyancy of bubbles.

* * * * *